(12) United States Patent
Yoon et al.

(10) Patent No.: US 9,427,164 B2
(45) Date of Patent: Aug. 30, 2016

(54) INSERTABLE NEURAL PROBE WITH FLEXIBLE STRUCTURE

(75) Inventors: Euisik Yoon, Ann Arbor, MI (US); Fan Wu, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 123 days.

(21) Appl. No.: 14/096,879

(22) PCT Filed: Jun. 4, 2012

(86) PCT No.: PCT/US2012/040709
§ 371 (c)(1),
(2), (4) Date: Mar. 27, 2014

(87) PCT Pub. No.: WO2012/170340
PCT Pub. Date: Dec. 13, 2012

(65) Prior Publication Data
US 2014/0288458 A1    Sep. 25, 2014

Related U.S. Application Data

(60) Provisional application No. 61/493,442, filed on Jun. 4, 2011.

(51) Int. Cl.
*A61B 5/04*    (2006.01)
*A61N 1/05*    (2006.01)
*A61B 5/0478*  (2006.01)
(Continued)

(52) U.S. Cl.
CPC ......... *A61B 5/04001* (2013.01); *A61B 5/0478* (2013.01); *A61B 5/40* (2013.01); *A61L 29/148* (2013.01); *A61N 1/0529* (2013.01);
(Continued)

(58) Field of Classification Search
CPC ............ A61B 5/04001; A61B 5/0478; A61N 1/0551
USPC ................................... 600/377, 378; 607/116
See application file for complete search history.

(56) References Cited

U.S. PATENT DOCUMENTS 5,900,245 A    5/1999  Sawhney et al.
6,091,979 A *  7/2000  Madsen ........................ 600/377
(Continued)

OTHER PUBLICATIONS

R.J. Vetter et al. "Chronic Neural Recording Using Silicon-Substrate Microelectrode Arrays Implanted in Cerebral Cortex", IEEE Transactions on Biomedical Engineering, vol. 51, No. 6, pp. 896-904, Jun. 2004.

(Continued)

*Primary Examiner* — Lee S Cohen
(74) *Attorney, Agent, or Firm* — Reising Ethington P.C.

(57) ABSTRACT

A neural probe (10) is provided for in vivo communication with biological tissue, including stimulating neurons and/or recording neural electrical activity. The probe (10) may be constructed so that the immune response by the biological tissue in which the device is implanted is reduced over known implantable probes. The probe (10) can be constructed with a tip (16) that has a branched configuration, with electrodes (24) located along each of the branches (20). A biodegradable coating (18) is disposed over at least the tip (16) of the probe (10) to provide the probe (10) with sufficient integrity for insertion into the biological tissue and to degrade after insertion. The biodegradable coating (18) can have an anti-inflammatory drug or other bioagent distributed therein for localized release of the bioagent to further reduce the immune response.

20 Claims, 8 Drawing Sheets

(51) Int. Cl.
  *A61B 5/00*  (2006.01)
  *A61L 29/14* (2006.01)
  *A61N 5/06*  (2006.01)
  *A61N 1/36*  (2006.01)

(52) U.S. Cl.
  CPC .......... *A61N1/0551* (2013.01); *A61N 5/0622* (2013.01); *A61N 1/3605* (2013.01)

(56) References Cited

U.S. PATENT DOCUMENTS

| | | | | |
|---|---|---|---|---|
| 6,829,498 | B2* | 12/2004 | Kipke et al. | 600/378 |
| 7,774,053 | B2 | 8/2010 | Garell et al. | |
| 8,386,006 | B2* | 2/2013 | Schouenborg | 600/373 |
| 8,442,614 | B2* | 5/2013 | Schulman | 600/378 |
| 8,798,737 | B2* | 8/2014 | Merz et al. | 607/2 |
| 8,870,857 | B2* | 10/2014 | Seymour | A61B 5/0084 600/342 |
| 2005/0216072 | A1 | 9/2005 | Mahadevan-Jansen et al. | |
| 2006/0030833 | A1 | 2/2006 | Harris et al. | |
| 2008/0255439 | A1 | 10/2008 | Tang et al. | |
| 2009/0299167 | A1 | 12/2009 | Seymour | |
| 2010/0256746 | A1 | 10/2010 | Taylor et al. | |
| 2010/0331935 | A1 | 12/2010 | Tabada et al. | |
| 2011/0230747 | A1* | 9/2011 | Rogers et al. | 600/377 |
| 2013/0079615 | A1* | 3/2013 | Yoon et al. | 600/377 |

OTHER PUBLICATIONS

X. Liu et al., "Stability of the Interface Between Neural Tissue and Chronically Implanted Intracortical Microelectrodes", IEEE Transactions on Rehabilitation Engineering, vol. 7, No. 3, pp. 315-326, 1999.

Y-T. Kim et al., "Chronic Response of Adult Rat Brain Tissue to Implants Anchored to the Skull", Biomaterials, vol. 25, pp. 2229-2237, 2004.

V. Polikov et al., "Response of Brain Tissue to Chonically Implanted Neural Electrodes", Journal of Neuroscience Methods, vol. 148, pp. 1-18, 2005.

K. K. Lee et al., "Polyimide-Based Intracortical Neural Implant with Improved Structural Stiffness", Journal of Micromechanics and Microengineering, vol. 14, pp. 32-37, 2004.

J. Seymour et al., "Fabrication of Polymer Neural Probes with Sub-cellular Features for Reduced Tissue Encapsulation", EMBS Annual International Conference, New York City, NY, 2006, pp. 4606-4609.

M. Merriam "A Three-dimensional Bidirectional Interface for Neural Mapping Studies," Ph.D. Dissertation, Dept. of Electrical Engineering, University of Michigan, Ann Arbor, MI, 2010.

H. Jin et al.., "Water-Stable Silk Films with Reduced β-Sheet Content", Advanced Functional Materials, vol. 15, pp. 1241-1247, 2005.

International Search Report for application No. PCT/US2012/040709, dated Dec. 21, 2012, 6 pages.

* cited by examiner

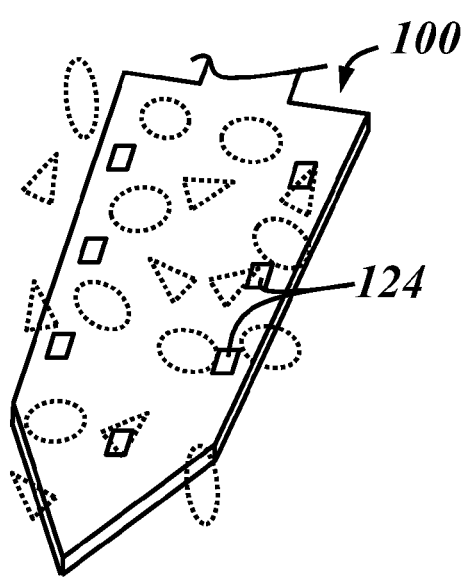 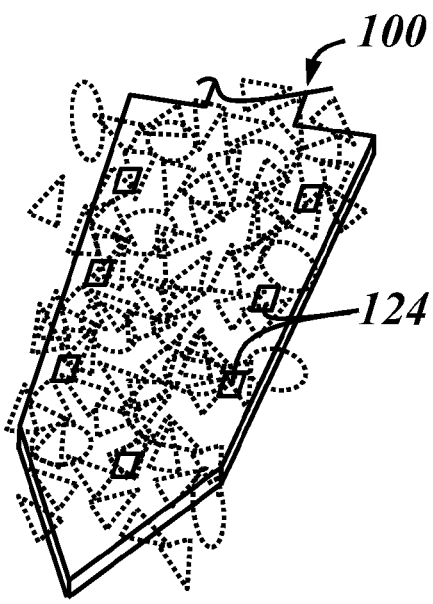
*FIG. 7A*      *FIG. 7B*
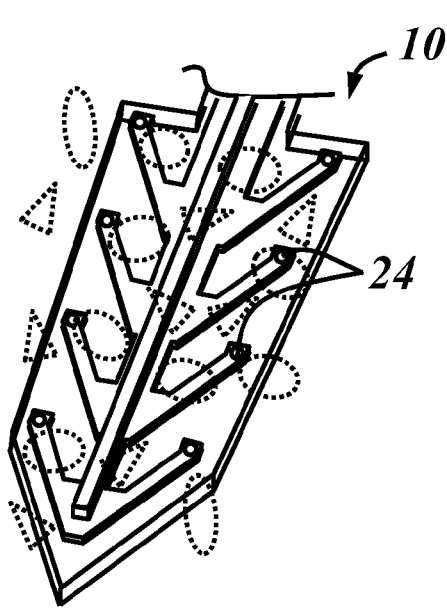 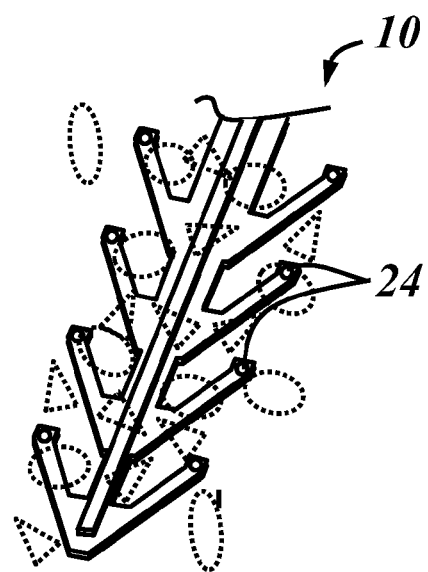
*FIG. 7C*      *FIG. 7D*

INSERTABLE NEURAL PROBE WITH FLEXIBLE STRUCTURE

TECHNICAL FIELD

This disclosure relates generally to biocompatible devices for implantation or insertion into biological tissue and, more specifically, to neural probes.

BACKGROUND OF THE INVENTION

Chronic neural recording has long been challenged by the inevitable immune response that can degrade the quality of the recorded signals over time. Implanted probes can damage the surrounding neurons, and glial scar formation due to the immune response may sometimes completely extinguish the functionality of implanted neural probes by encapsulating the recording electrodes. Certain implant characteristics may help reduce the immune response, such as high flexibility, small size, and large separation gaps between structures. However, some of these characteristics can also decrease the mechanical stiffness of the device and render the surgical process of implantation impractical—i.e., the device is too flexible to penetrate the desired tissue. Some methods require cutting an insertion path with a surgical tool prior to the insertion of flexible implants. This can severely damage the target tissue and risk deforming the flexible implant during implantation so that relative positioning of the recording sites may be distorted.

SUMMARY

According to one embodiment, there is provided a neural probe, including a body, a tip, and a shank extending from the body to the tip. The neural probe includes one or more electrodes supported by the tip for stimulating neurons, recording neural electrical activity, or both. A biodegradable coating is disposed over the tip, and the coating has a stiffness that is higher than a stiffness of the shank.

According to another embodiment, there is provided a neural probe, including a body, a tip, and a shank extending from the body to the tip. The tip includes a plurality of branches. The neural probe includes one or more electrodes supported by the tip for stimulating neurons, recording neural electrical activity, or both. At least one of the electrodes is located along one of the branches.

According to another embodiment, there is provided an implantable device for in vivo communication with biological tissue. At least a portion of the device is coated with a biodegradable material, and the device is non-operable until the biodegradable material substantially degrades.

BRIEF DESCRIPTION OF THE DRAWINGS

Exemplary embodiments will hereinafter be described in conjunction with the appended drawings, wherein like designations denote like elements, and wherein:

FIG. 7A is a schematic view of a non-branched silicon probe just after implantation;

FIG. 7B is a schematic view of the probe of FIG. 7A about 6 weeks after implantation, showing the predicted immune response;

FIG. 7C is a schematic view of the probe of FIG. 6 just after implantation;

FIG. 7D is a schematic view of the probe of FIG. 6 about 6 weeks after implantation, showing the predicted immune response;

DETAILED DESCRIPTION OF THE ILLUSTRATED EMBODIMENTS

Disclosed below are structures and methods that may be useful to allow neural probes or other medical implants to be designed with a nearly limitless number of materials and/or geometries. According to one embodiment, one or more portions of a neural probe may be coated with a biodegradable polymer that temporarily provides certain probe components with a mechanical stiffness that is sufficiently high for insertion into the desired biological tissue. The biodegradable material may begin degrade after insertion and completely degrade thereafter. According to the exemplary methods and structures disclosed herein, the available options for useful neural probe geometry and materials may be significantly broadened to include geometries and materials that can help optimize in vivo recording quality and probe lifetime. Material choice and miniaturization of any biomedical implantable device is no longer limited by the mechanical stiffness required to penetrate the desired tissue. The structures and methods disclosed below are not limited to neural probes, as they are also applicable to any chronic implantable device that will benefit from having significantly increased design freedom regarding material selection and geometry.

Figures 1, 2:
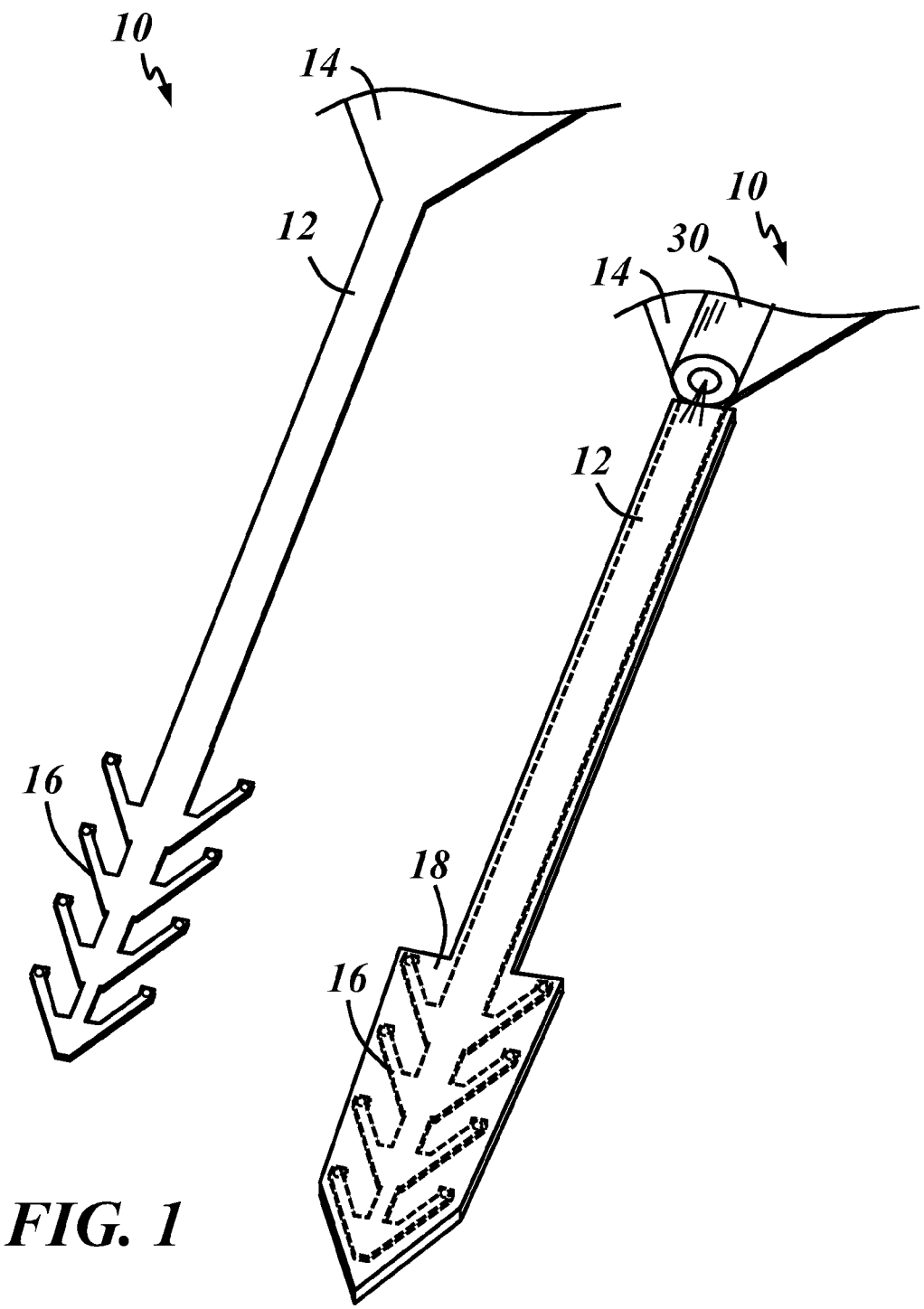
FIG. 1 is a perspective view of a neural probe including a branched tip, according to one embodiment.
FIG. 2 is the neural probe of FIG. 1, shown with a coating over portions of the probe.

Referring to FIGS. 1 and 2, there is shown an exemplary neural probe 10 that includes a shank 12 that extends from a probe body 14 to a tip 16. The probe 10 may include a biodegradable coating 18 disposed over at least a portion of the shank 12 and/or the tip 16. FIG. 1 shows the probe 10 without the coating 18, and FIG. 2 shows the probe 10 with the coating 18 disposed over the entire tip 16 and generally the entire shank 12. In one embodiment, the portion of the probe 10 intended for implantation into biological tissue is fully encapsulated by the biodegradable coating 18. The stiffness of the coating 18 may be higher than the stiffness of the shank 12, meaning that more force is required to deform or deflect the coating 18 a given amount than is required for the shank 12. As shown in FIG. 2, the probe 10 may also include an optional light source 30. The light source 30 may provide neuron-affecting light at the probe tip to stimulate or silence neurons. In this example, the light source 30 is an optical fiber attached at the probe body 14. The light source may be located at or near the probe body or shank for optical stimulation of neurons coupled with optogenetics techniques. The positioning of the optical fiber can be controlled by patterning grooves on the probe surface(s) such as the body 14 or shank 12.

Figure 3:
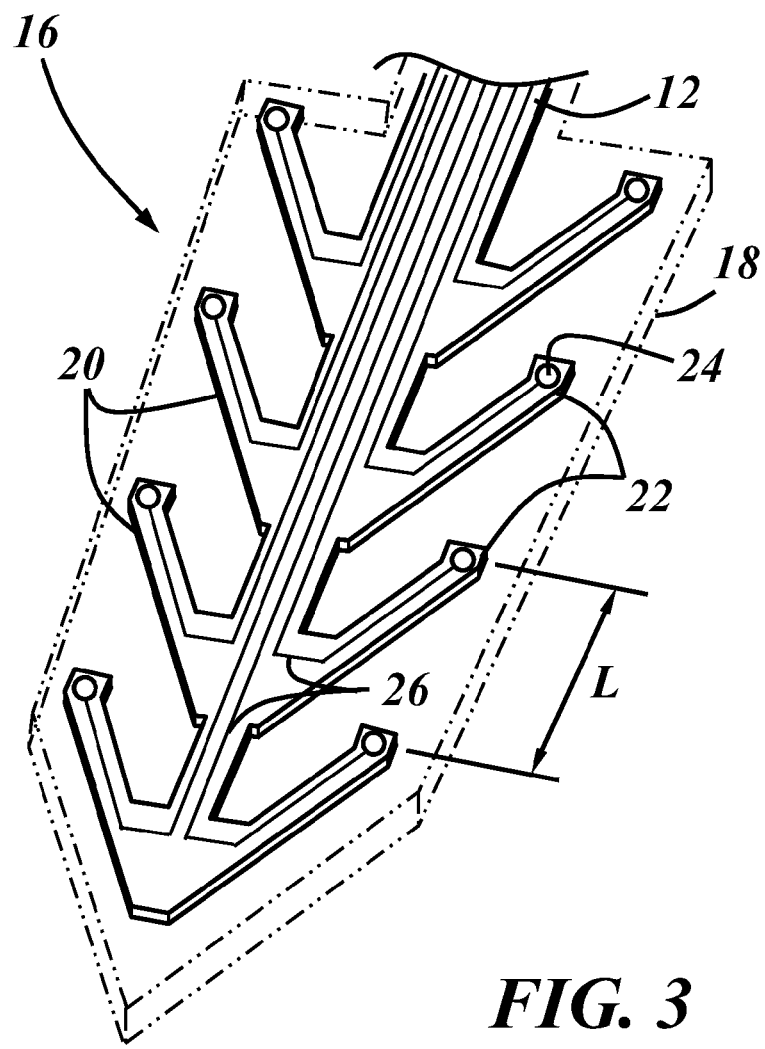
FIG. 3 is an enlarged view of FIG. 2, showing the branched tip of the probe.

FIG. 3 is an enlarged view of the tip 16 of FIG. 2 with the coating 18 shown in phantom. The tip 16 may include a plurality of branches 20 with ends 22 that are spaced apart from one another as shown. One or more electrodes 24 for recording neural electrical activity or stimulating neurons may be located anywhere along the shank 12 and/or tip 16, including along the length of any branch 20 or at the end 22 of any branch. A recording site may be defined by the location of each recording electrode 24. Each electrode 24 can be constructed from iridium or any other suitable electrode material. The number of recording sites can be as high as desired to simultaneously monitor individual neural activities from a complex neural network. The branches or side-arms 20 of the illustrated tip 16 are arranged in a herringbone configuration, with each branch 20 extending toward its respective end 22 at a non-perpendicular angle with respect to the shank 12. A branched tip configuration may help minimize chronic immune response near the electrodes 24. The branches 20 need not be in a herringbone configuration to achieve this or other advantages. In one embodiment, each branch 20 has a width in a range from about 10-20 µm. In one specific embodiment, each branch is about 14 µm wide, and there is an electrode 24 at or near the end 22 of each branch.

The usable life of the electrodes 24 may be significantly prolonged compared to electrodes of other types of probes. For example, the only foreign objects in the vicinity of the electrodes 24 in the configuration of FIG. 3 are the narrow branch structures that support electrical interconnections 26, along which the electrodes electrically communicate with other components at the probe body 14 or elsewhere. Though visible here, the interconnections 26 may be at least partly encapsulated in shank and/or tip material. The electrodes 24 can be sized so that they may be nearly invisible to the immune system, as minimal tissue reactions may occur near structures with sub-cellular dimensions. For example, each electrode 24 may have a width in a range from about 5 µm to about 15 µm, and preferably less than 10 µm, depending partly on the width of the respective branch 20. In one embodiment, the width of the electrode 24 of a given branch 20 has a width that is about 50% to about 100% of the width of the branch 20. The relatively large shank 12, which may range in width from 50-100 µm, or be at least wide enough to accommodate the multiple electrical interconnections 26 between the electrodes 24 and the probe body 14, is spaced from the electrodes 24 by a relatively large distance due to the electrode locations being at the ends 22 of the branches 20. In one non-limiting example, each electrode 24 is spaced from the shank 12 by about 100 µm. As a result, even if glial scarring occurs at the probe shank region, the remotely located electrodes 24 may not be affected. Further, the spacing between adjacent branches in the illustrated embodiment may enhance the through-probe diffusion of biochemicals which, if adsorbed onto the probe surface, could initiate a cascade of reactions toward a fully mobilized immune response. In one non-limiting example, the spacing between adjacent branches, illustrated as L in FIG. 3, is about 180 µm.

The probe 10, particularly the shank 12 and the tip 16, may be constructed using flexible and biocompatible materials, such as polyimide, parylene, liquid crystal polymer (LCP) or other suitable materials. These types of materials can allow the implanted probe 10 to sway or move in sync with the micromotion of the brain or other tissue in which it is inserted and may reduce the amount of tissue damage caused by shear stresses. Material selection may be based partially on other factors as well, such as fabrication process compatibility, Young's modulus, moisture absorption and/or biocompatibility and may further depend on the requirements of a specific application. In some embodiments, the biodegradable coating 18 may electrically or otherwise isolate the recording or stimulus electrodes 24 from surrounding tissue or from other portions of the probe 10, whereby the probe will be non-operable until the coating at least partially degrades.

Figure 4:
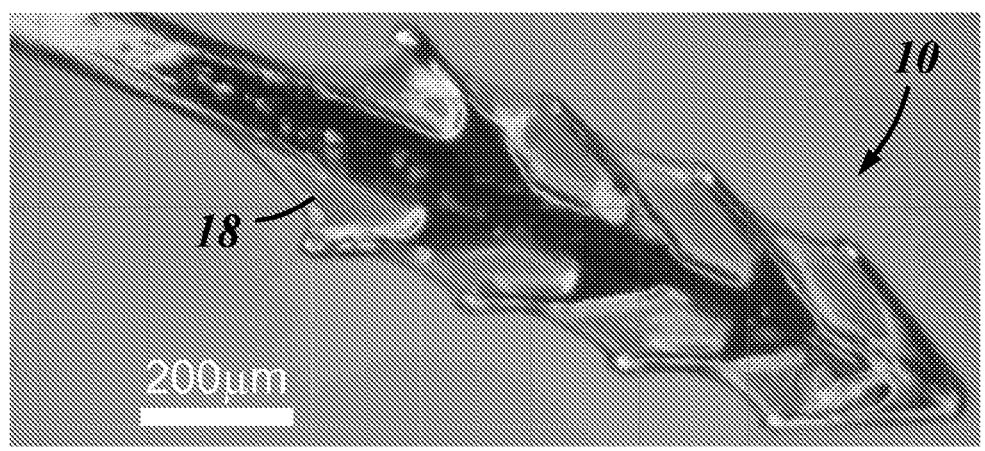
FIG. 4 is a photographic image of an illustrative probe, where the coating is applied via a dip-coating process.
Figure 5:
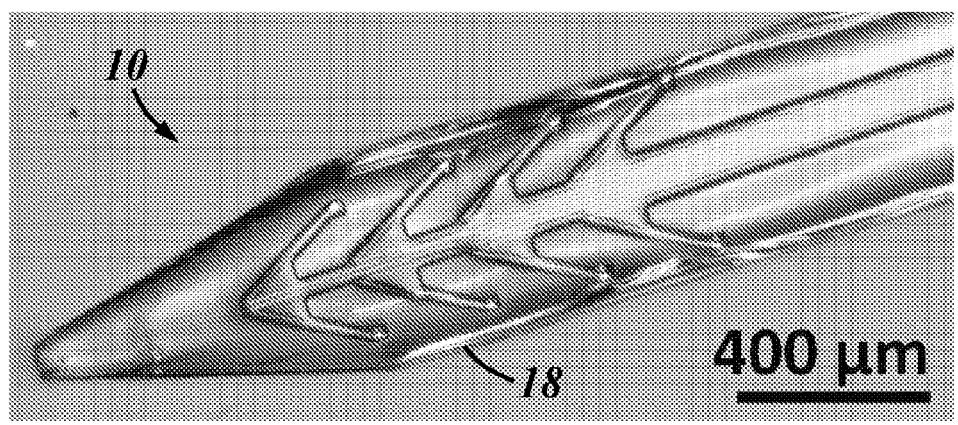
FIG. 5 is a photographic image of another illustrative probe, where the coating is applied via a micro-molding process.

While the flexible branched-tip configuration shown in the previous figures may be useful to reduce chronic tissue reaction near the electrodes 24 for at least the above-described reasons, the high flexibility of such a configuration may prevent insertion into biological tissue. As used herein, "high flexibility" when referring to the probe 10, its components, or component materials is used to indicate level of flexibility that is sufficiently high that it prevents or significantly hinders probe insertion into the desired tissue—i.e., the probe 10 will bend, buckle, or collapse rather than penetrate the tissue when made using highly flexible materials. The biodegradable coating 18 may provide the necessary mechanical stiffness or integrity for insertion. The coating 18 may be polymeric or may be another type of biodegradable material and may be selected to degrade relatively quickly once probe insertion is complete, thereby exposing the underlying probe components to the surrounding tissue. The material(s) for coating 18 may be selected based on a number of criteria including stiffness, degradation rate, process compatibility and/or biocompatibility, to name a few. In one embodiment, the biodegradable coating 18 is Silk-I protein polymer derived from the *Bombyx mori* cocoon. The feasibility of this material has been demonstrated experimentally. Other possible coating materials include poly-lactic-co-glycolic acid (PLGA), Chitosan, collagen, or any other biodegradable material. The coating 18 can be applied over the desired portions of the shank 12 and/or tip 16 by dip-coating, soft-lithography, laser machining, or other suitable methods. In one embodiment, the coating 18 is applied via a PDMS micro-molding process. The coating 18 fills the regions between the narrow branches 20, making the tip 16 structure more rigid overall. FIG. 4 is a photographic image of an illustrative probe 10 with the coating 18 applied via a dip-coating process, and FIG. 5 is a photographic image of an illustrative probe 10 with the coating 18 applied via a micro-molding process.

Figure 6:
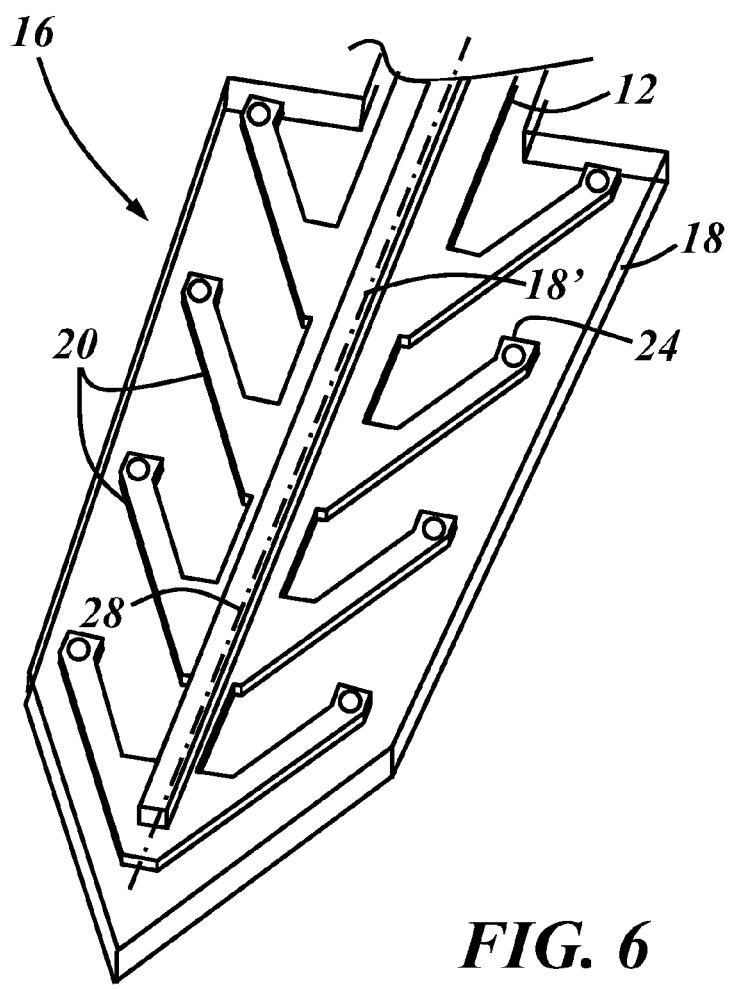
FIG. 6 is an enlarged view of the tip of another embodiment of a neural probe with a portion of the coating configured for bioagent delivery.

In some embodiments, drugs or other bioagents, such as anti-inflammatory drugs or neuronal growth factors, may be incorporated into the biodegradable coating 18 to further reduce immune system response. Such bioagents can be distributed throughout the coating 18 for release upon coating degradation, or bioagents may be included with only a portion of the coating 18. For example, multiple types of biodegradable coating materials can be patterned during probe construction to control the drug release type, timing and rate. FIG. 6 illustrates a probe 10 with a biodegradable coating 18 that includes a slow-degrading portion 18' located along a centerline 28 of the probe. The electrical interconnections are omitted from FIG. 6 for clarity. The slow-degrading portion 18' includes a relatively slow-degrading polymer coated along the probe shank 12 and/or the center of the tip 16 for chronic drug delivery, while the remainder of the coating 18 is made from a relatively fast-degrading polymer. The coating portion 18' may be encapsulated within the remainder of the coating 18—i.e., the faster-degrading material may be applied over the top of portion 18'—or the slow-degrading portion 18' may form a portion of the exterior surface of the probe. It is also possible to use multiple biodegradable polymers on the probe to release different drugs at different rates. The biodegradable material used for drug delivery may be the same or different from the biodegradable coating used to increase the stiffness of the probe, and it may cover a smaller portion of the underlying probe components.

FIGS. 7A-7D illustrate a comparison between the expected tissue reaction to a silicon probe 100 with a non-branched tip (shown in FIGS. 7A-7B) and the probe 10 with the tip configuration of FIG. 6 (shown in FIGS. 7C-7D). The dotted oval shapes represent neurons, and the dotted triangle shapes represent astrocyte/microglia. FIG. 7A shows the silicon probe 100 just after implantation, and FIG. 7B shows the silicon probe almost completely encapsulated by glial scarring approximately 6 weeks after implantation, thereby insulating the electrodes 124 from the neural potentials. FIG. 7C shows the probe 10 from FIG. 6 just after implantation, and FIG. 7D shows the predicted reduced immune response to probe 10 after 6 weeks, where the overall astrocyte/microglia density is relatively reduced near the implanted branched-tip probe 10 due at least partly to the anti-inflammatory drug effect. Even if mild glial scar formation is observed at the probe shank, the electrodes 24 may remain unaffected due to their location at the ends of the tip branches.

Figure 8:
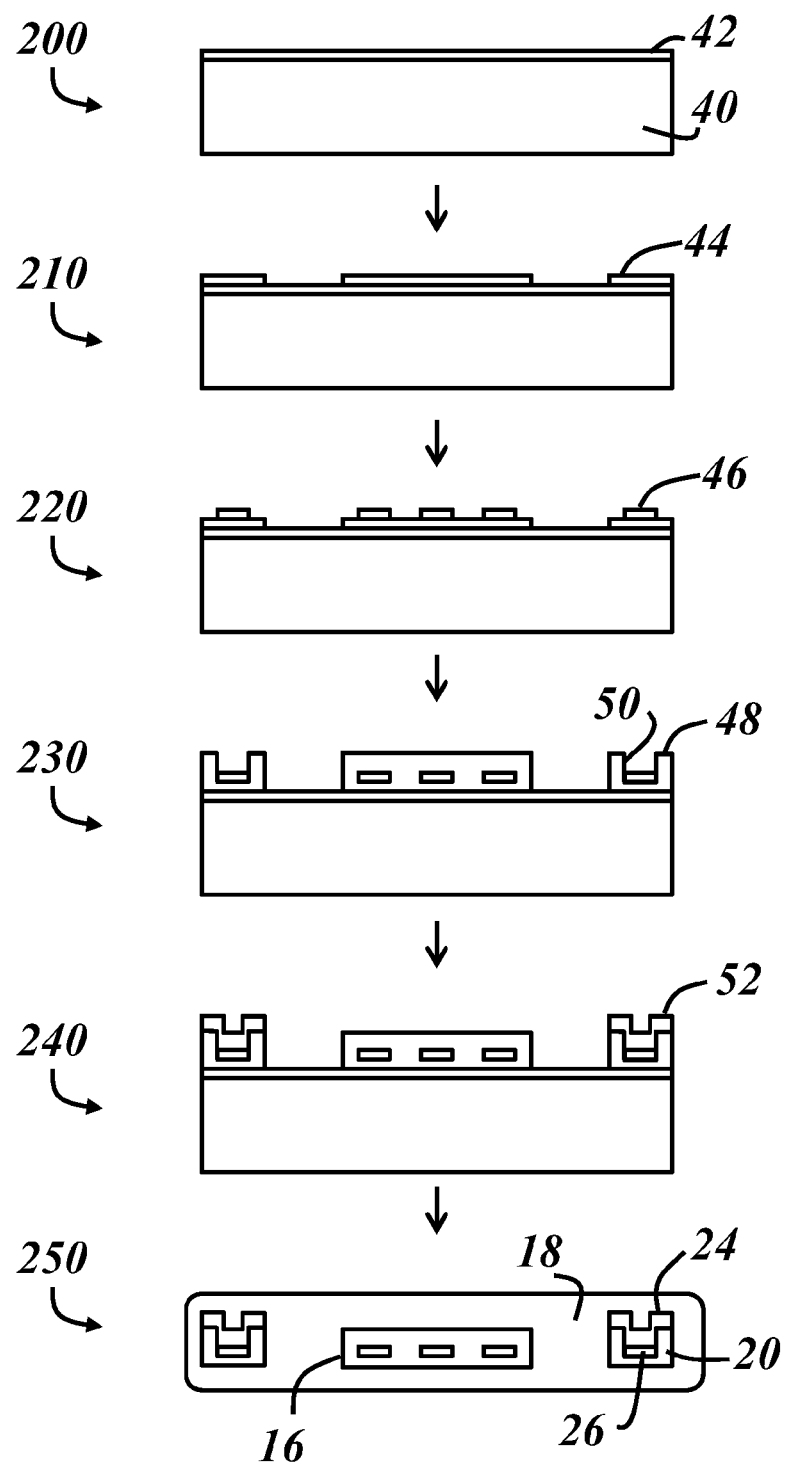
FIG. 8 illustrates an exemplary method of making a probe, according to one embodiment.

A cross-sectional view of one embodiment of a probe fabrication process is shown in FIG. 8. The cross-section is taken through the probe tip and through electrodes on each side of the tip. In this embodiment, sacrificial Cr/Au/Cr layers 42 are evaporated onto a glass wafer 40 in step 200 for use in a release step prior to a final coating step 250. In step 210, photo-definable polyimide is lithographically patterned to form a bottom substrate layer 44. The bottom substrate layer 44 becomes part of the tip 16 of the finished probe in the views shown, as well as part of the shank. In step 220, a layer of Ti/Au 46 is evaporated over the bottom substrate layer 44 to form the electrical interconnections 26. In step 230, a top polyimide layer 48 is selectively patterned to cover the interconnections 26, leaving exposed Ti/Au at the electrode and bonding pad sites and surrounding each electrode location with a generally vertical sidewall 50. Next, in step 240, a layer 52 of Ti/Ir is sputtered to form the recording electrodes 24. The device is then released in Cr etchant, and the desired portion(s) of the fabricated device are coated with the biodegradable coating 18 in step 250. Of course, additional method steps may be included or other suitable materials may be used, as this is only one specific example of a process that may be used to form a neural probe. Apart from recording electrodes, stimulation electrodes can be provided using materials such as using iridium oxide, and these can be provided in lieu of the recording electrodes or in addition to the recording electrodes so that both stimulation and passive recording can be performed.

Figure 9:
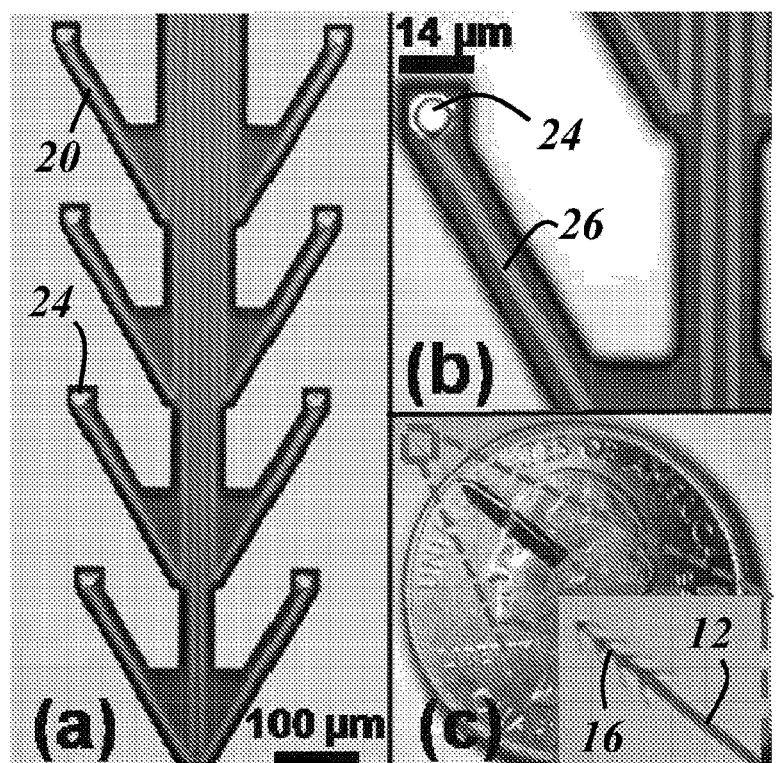
FIG. 9 includes photomicrographs of an exemplary probe fabricated by the method shown in FIG. 8, including: (a) the tip of the probe before application of the biodegradable coating, (b) a tip branch with an electrode, and (c) the full probe positioned over a U.S. quarter to demonstrate dimensional scale.
Figure 10:
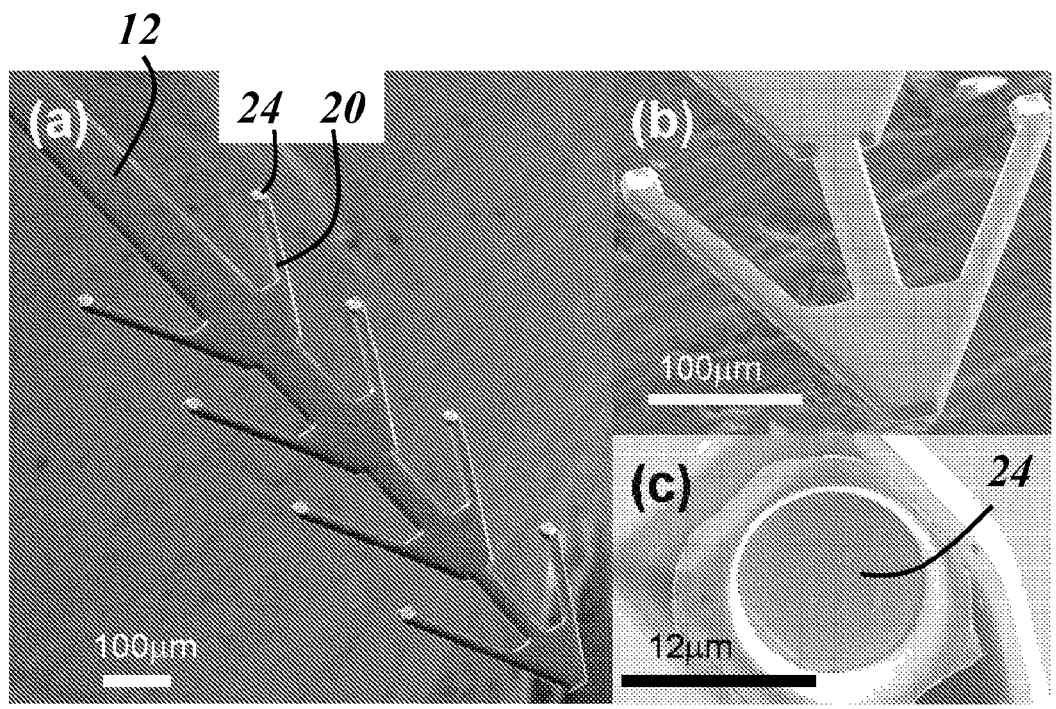
FIG. 10 includes SEM images of another exemplary probe fabricated by the method shown in FIG. 8, including: (a) the shank and tip of the probe before application of the biodegradable coating, (b) two tip branches with electrodes, and (c) an enlarged view of one of the electrodes.

FIGS. 9 and 10 are respective microscopic and SEM images of a polyimide probe constructed using the method of FIG. 8 prior to the final coating step 250. The probe shank 12 and the branches 20 are straight as a result of stress-free composite layers. FIG. 10 shows the conformal coverage of one of the Ir electrodes 24 over a 5 μm step between the top and bottom polyimide layers. The coverage over the vertical polyimide sidewall more than doubles the electrode area in the illustrated layout, when compared with a flat electrode of the same width or diameter. This can reduce the electrode impedance to approximately 400 kΩ at 1 kHz, which may be useful for high signal-to-noise ratio neural recording.

Figure 11:
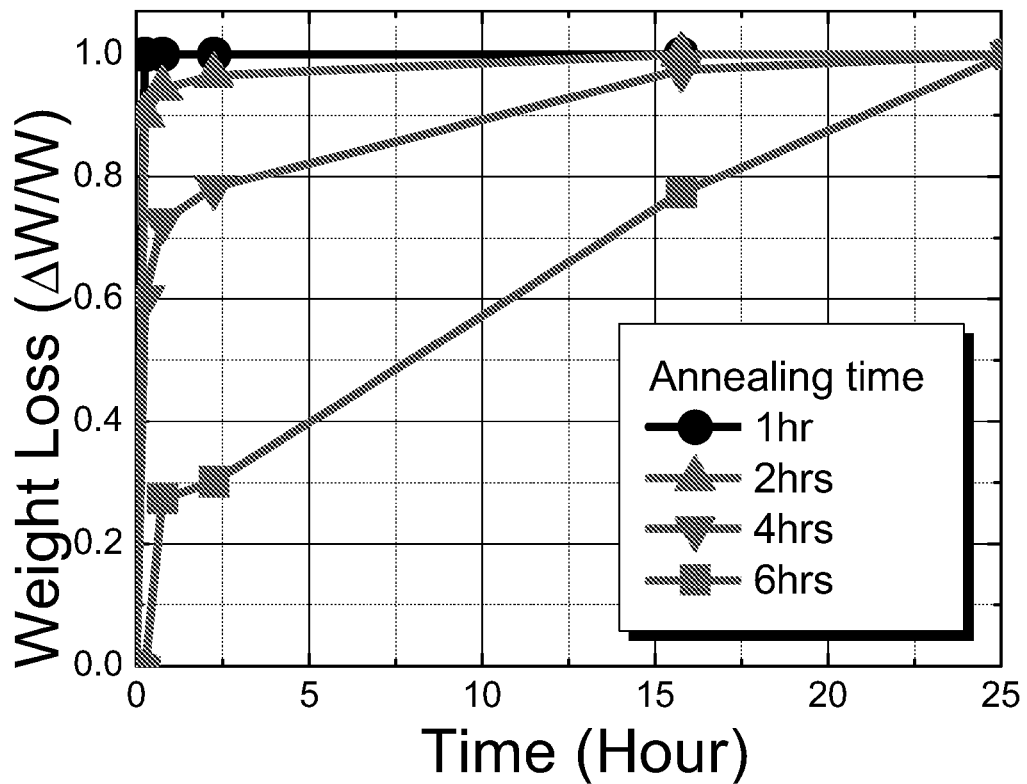
FIG. 11 is a chart showing the rate of degradation of a biodegradable coating material subjected to different annealing times.

A degradation rate for the biodegradable coating may be characterized in protease solution to simulate enzyme-facilitated degradation that occurs in vivo. Samples of silk films were treated with a water annealing process (described by Jin et al. in "Water-Stable Silk Films with Reduced β-Sheet Content," *Adv. Funct. Mat.*, 15:1241-1247 (2005)), to alter the protein structures. The weight loss of the silk samples over time is shown in FIG. 11. The degradation rate is shown to be inversely related to the water annealing time. The degradation rate of the coating 18 may thus be tailored according to the needs of a specific in vivo application. For example, fast degradation of the biodegradable coating 18 can quickly expose the electrodes to surrounding neurons. In some cases, it may be desirable to delay the coating degradation, such as in instances where the insertion process requires a longer time to complete or when chronic drug release is desired from or through the coating.

Figure 12:
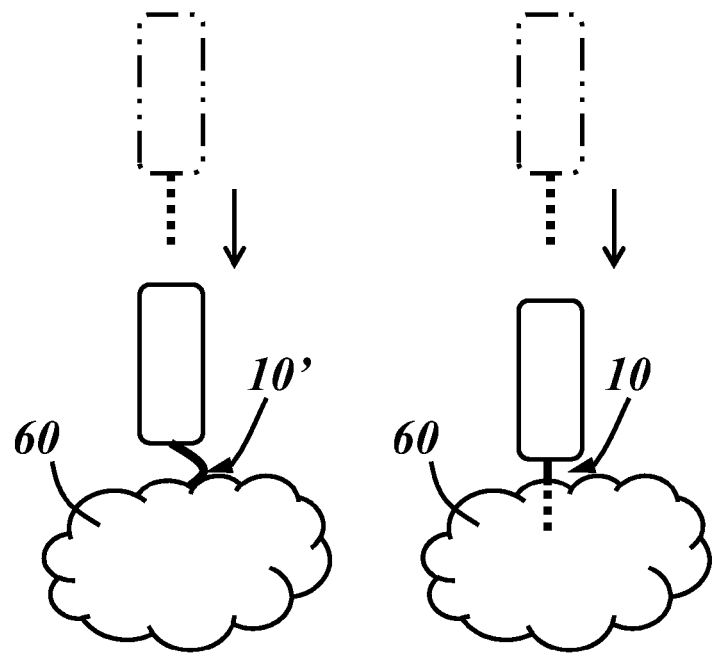
FIG. 12 is a schematic representation of experiments demonstrating the comparative stiffness of probes with and without the biodegradable coating.

In FIG. 12, the mechanical stiffness of a polyimide probe 10 having a biodegradable silk coating is compared with a bare polyimide probe 10'. FIG. 12 illustrates actual experiments conducted with coated and uncoated polyimide probes, with the results depicted schematically here for clarity. Each probe 10 and 10' was bonded to a PCB and lowered by a micromanipulator in an attempt to insert the probe into fish brain tissue 60. As shown, the highly flexible, uncoated polyimide probe 10' bends and does not penetrate the tissue, as its shank lacks sufficient mechanical stiffness. Probe 10, which includes biodegradable coating—silk in this example—is sufficiently rigid to penetrate the tissue as shown. Thus, probes constructed as described above can facilitate insertion of a neural probe without the aid of additional surgical tools.

Figure 13:
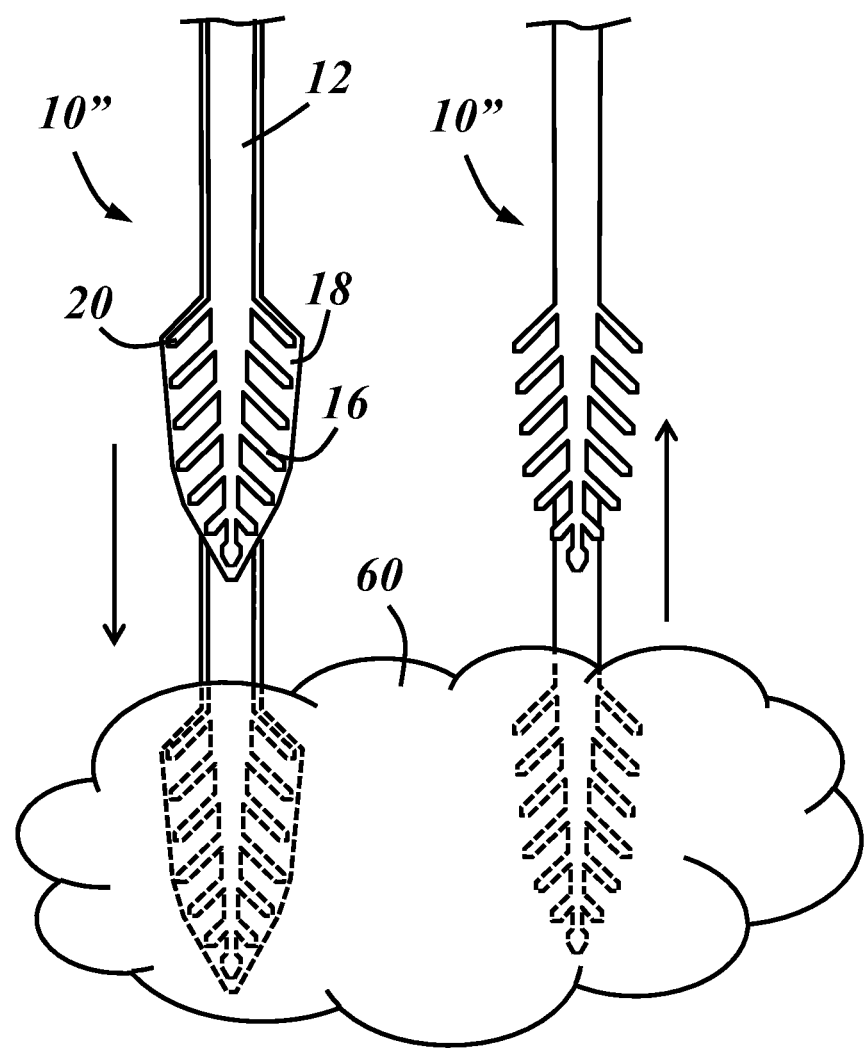
FIG. 13 is a schematic representation of another embodiment of a probe having a branched tip with a reverse-herringbone configuration, shown inserted and removed from tissue.

FIG. 13 illustrates another embodiment of a neural probe 10" having a branched tip 16. The branch orientation in this example is different from the branch orientation of the previously described embodiments. In this example, each of the branches 20 extends in a direction generally toward the front of the probe or away from the probe body, whereas the branches of the earlier-described herringbone configurations extend in a direction generally toward the rear of the probe or toward the probe body. The example of FIG. 13 is also a herringbone configuration, but may be referred to as a reverse-herringbone configuration for purposes of this description. The reverse-herringbone configuration may enable the implantable probe 10" to be removed from the biological tissue 60 as shown with minimal tissue damage, even after the coating 18 has degraded. The left side of FIG. 13 shows the probe 10" after insertion into the tissue 60 in the downward direction, and the right side of FIG. 13 shows the probe 10″ after removal from the tissue 60 in the upward direction.

The above-described probes may also include a light source 30 to provide neuron-affecting light at the probe tip to stimulate or silence neurons. As shown in FIG. 2, for example, an optical fiber can be attached at or near the probe body or shank for optical stimulation of neurons coupled with optogenetics techniques. The positioning of the optical fiber can be precisely controlled by patterning grooves on the probe surface(s) such as the body or shank. Though the relatively large size of the optical fiber may cause some damage to surrounding tissue, the neurons near the recording electrodes may avoid any harm caused by the optical fiber due to their remote location relative to the optical fiber, such as at the ends of the tip branches. Thus, simultaneous optical stimulation and electrical recording by a flexible polymer neural probe for enhanced biocompatibility in chronic in-vivo studies may be provided.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A neural probe (10), comprising:
 a body (14), a tip (16), and a shank (12) extending from the body (14) to the tip (16), the tip (16) comprising a plurality of branches (20), wherein each branch (20) extends straight from the shank (12) to a respective branch end (22) at a non-perpendicular angle with respect to the shank (12), and at least one branch (20) of the plurality of branches is located at the same lengthwise portion of the shank (12) as another branch (20) of the plurality of branches;
 one or more electrodes (24) supported by the tip (16) for stimulating neurons, recording neural electrical activity, or both; and
 a biodegradable coating (18) disposed over the tip (16), the coating (16) having a stiffness that is higher than a stiffness of the shank (12).

2. A neural probe (10) as defined in claim 1, wherein at least one of said electrodes (24) is located along one of the branches (20).

3. A neural probe (10) as defined in claim 1, wherein the biodegradable coating (18) is disposed over at least a portion of the shank (12).

4. A neural probe (10) as defined in claim 1, further comprising:
 a bioagent distributed within at least a portion of the biodegradable coating (18).

5. A neural probe (10) as defined in claim 4, wherein the bioagent is distributed within a slow-degrading portion (18′) of the biodegradable coating (18) that degrades slower than another portion of the biodegradable coating (18).

6. A neural probe (10) as defined in claim 5, wherein the slow-degrading portion (18′) of the coating is at least partly located along a centerline (28) of the probe (10).

7. A neural probe (10) as defined in claim 1, wherein the biodegradable coating (18) comprises silk.

8. A neural probe (10) as defined in claim 1, wherein each of said branches (20) supports said one or more electrodes (24) at each respective end (22), wherein the plurality of branches (20) is arranged in a herringbone configuration having a pair of branches (20) extending from the tip (16) toward the body (14) and forming an angled configuration at the tip (16) with a plurality of other branches (20) extending from the shank (12) toward the body (14).

9. A neural probe (10) as defined in claim 8, wherein the biodegradable coating (18) conforms to the angled configuration at the tip (16).

10. A neural probe (10), comprising:
 a body (14), an angled tip (16), and a shank (12) extending from the body (14) to a distal end of the angled tip (16), the tip (16) having a branched tip configuration comprising a plurality of branches (20) near the distal end of the angled tip, said branches (20) extending out from the shank to define at least a portion of an outer perimeter of the tip (16); and
 one or more electrodes (24) supported by the tip for stimulating neurons, recording neural electrical activity, or both, wherein at least one of the electrodes (24) is located along one of the branches (20).

11. A neural probe (10) as defined in claim 10, wherein each branch (20) extends to a respective branch end (22) at a non-perpendicular angle with respect to the shank (12).

12. A neural probe (10) as defined in claim 10, wherein the plurality of branches (20) is arranged in a herringbone configuration.

13. A neural probe (10) as defined in claim 10, wherein at least one of said electrodes (24) is located at an end (22) of each branch (20).

14. A neural probe (10) as defined in claim 10, further comprising:
 a biodegradable coating (18) disposed over each of said electrodes (24).

15. A neural probe (10) as defined in claim 10, further comprising:
 a light source (30) for providing neuron-affecting light at said tip.

16. A neural probe (10) as defined in claim 10, wherein the shank (12) and the plurality of branches (20) comprise straight, stress-free composite layers.

17. A neural probe (10) as defined in claim 10, wherein each branch (20) has a width in a range from about 5 μm to 15 μm and the shank has a width in a range from about 50 μm to 100 μm.

18. A neural probe (10) as defined in claim 10, further comprising a plurality of electrical interconnections (26), wherein the plurality of electrical interconnections (26) extend from the body (14) to each of said one or more electrodes (24), wherein the shank (12) includes the plurality of electrical interconnections (26) and each branch of the plurality of branches (20) includes only one electrical interconnection (26) of the plurality of electrical interconnections (26).

19. An implantable device (10) for in vivo communication with biological tissue (60), comprising:
- a body (14), a branched tip (16), and a shank (12) extending from the body (14) to the branched tip (16), wherein the branched tip (16) includes a plurality of branches (20), each of said branches (20) extending to a respective end (22) and having an electrode (24) located at said respective end (22), wherein the plurality of branches (20) is arranged in a herringbone configuration having a pair of branches (20) extending from the tip (16) toward the body (14) and forming an angled configuration at the tip (16) with a plurality of other branches (20) extending from the shank (12) toward the body (14); and
- a biodegradable material (18) coating at least a portion of the branched tip (16) or the shank (12), wherein the device (10) is non-operable until the biodegradable material (18) substantially degrades.

20. An implantable device (10) according to claim 19, wherein the biodegradable material (18) is coated over each electrode (24) and substantially fills the space between adjacent branches (20).

\* \* \* \* \*